US006013231A

United States Patent [19]

Zaunbrecher et al.

[11] Patent Number: 6,013,231

[45] Date of Patent: *Jan. 11, 2000

[54] WICK COMPOSITION FOR AIR FRESHENER CANDLE PRODUCT

[75] Inventors: Judith R. Zaunbrecher, Racine, Wis.; Mary Beth Adams, Lake, Ill.; Luz P. Requejo, Racine, Wis.

[73] Assignee: S. C. Johnson & Son, Inc., Racine, Wis.

[ * ] Notice: This patent is subject to a terminal disclaimer.

[21] Appl. No.: 08/992,000

[22] Filed: Dec. 17, 1997

[51] Int. Cl.[7] .................... A61L 9/01; A61L 9/02

[52] U.S. Cl. .................... 422/126; 44/275; 44/519; 431/288

[58] Field of Search .................... 422/126, 4, 5; 44/275, 519; 431/288

[56] References Cited

U.S. PATENT DOCUMENTS

| | | |
|---|---|---|
| 1,974,037 | 9/1934 | Atkins . |
| 2,090,297 | 8/1937 | Knoche . |
| 2,379,250 | 6/1945 | Muskat et al. . |
| 2,415,040 | 1/1947 | Rust . |
| 2,818,615 | 1/1958 | Burness . |
| 2,829,511 | 4/1958 | Oesterle et al. . |
| 3,065,502 | 11/1962 | Lorenian . |
| 3,175,876 | 3/1965 | Fredericks . |
| 3,332,428 | 7/1967 | Mold et al. . |
| 3,351,695 | 11/1967 | Hollingworth . |
| 3,499,452 | 3/1970 | Kallianos et al. . |
| 3,560,122 | 2/1971 | Cassar . |
| 3,577,588 | 5/1971 | Chisholm . |
| 3,630,697 | 12/1971 | Duling et al. . |
| 3,705,890 | 12/1972 | Barker et al. . |
| 3,898,039 | 8/1975 | Lin . |
| 3,940,233 | 2/1976 | Fox et al. . |
| 4,092,988 | 6/1978 | Van Auken et al. . |
| 4,134,714 | 1/1979 | Driskill . |
| 4,155,979 | 5/1979 | Powell . |
| 4,278,658 | 7/1981 | Hooper et al. . |
| 4,302,409 | 11/1981 | Miller et al. . |
| 4,449,987 | 5/1984 | Lindauer . |
| 4,507,077 | 3/1985 | Sapper . |
| 4,568,270 | 2/1986 | Marcus et al. . |
| 4,663,315 | 5/1987 | Hasegawa et al. . |
| 4,708,851 | 11/1987 | Von Loringhoven . |
| 5,068,321 | 11/1991 | Buysch et al.. . |
| 5,069,231 | 12/1991 | Rutherford . |
| 5,081,104 | 1/1992 | Orson, Sr. . |
| 5,313,002 | 5/1994 | De Heij et al. . |
| 5,320,798 | 6/1994 | Chambon et al. . |
| 5,538,018 | 7/1996 | Chan et al. . |
| 5,569,799 | 10/1996 | Chen et al. . |
| 5,645,845 | 7/1997 | Neumann et al. . |

FOREIGN PATENT DOCUMENTS

| | | |
|---|---|---|
| 63-074440 | 4/1988 | Japan . |
| WO 99 08722 | 2/1999 | WIPO . |
| WO 99 09120 | 2/1999 | WIPO . |

OTHER PUBLICATIONS

Database WPI, Section Ch, Week 9033, Derwent Publication LTd., London, GB; Class C03 AN 90–250645, XP002086477 & JP 02 174628A (Dainippon Jochugiku KK).

Patent Abstracts of Japan, vol. 097, No. 011, Nov. 28, 1997 & JP 09 188893A (Unitika Ltd.).

Database WPI, Section Ch, Week, 8113, Derwent Publications Ltd. London, GB; Class D23 AN 81–22459D XP002039959 & JP 56 011994A (Kyoshin Co. Ltd.).

*Primary Examiner*—Elizabeth McKane

[57] ABSTRACT

This invention provides a wick composition which is comprised of a polymeric strand such as polyethylene, which has a content of particulate cellulosic filler ingredient. The cellulosic ingredient contains chemically-bound air-freshener constituent. The wick is adapted for incorporation in a candle body. When the wick is ignited, it combusts with a controlled release of the air freshener constituent into the atmosphere.

23 Claims, No Drawings

WICK COMPOSITION FOR AIR FRESHENER CANDLE PRODUCT

BACKGROUND OF THE INVENTION

This invention generally relates to the dispensing of an air freshener from a candle product. More specifically this invention relates to a wick composition having a content of air freshener constituent which is released under wick combustion conditions.

Candles have been known and used since early civilization. A typical candle is formed of a solid or semi-solid body of wax such as paraffin wax or beeswax, and it contains an axially embedded combustible fibrous wick.

When the wick of a candle is lit, the generated heat melts the solid wax, and the resulting liquid flows up the wick by capillary action and is combusted.

More recently candles have been developed that appeal to the olfactory as well as the visual sense. This type of candle usually incorporates a fragrance oil in the wax body. As the wax is melted in a lighted candle, there is a release of the fragrance oil from the liquified wax pool.

Conventional fragrance candles have drawbacks because of cost and other considerations. The incorporation of fragrance oil in candle wax is difficult to achieve in a quantity which ensures the release of a suitable level of fragrance into the atmosphere during candle burning. Further, the incorporated fragrance tends to migrate and volatilize from the wax body prematurely. The fragrance also softens the wax body, and there is an undesirable loss of rigidity in the candle structure.

There is continuing interest in the development of improved fragrance and other types of air freshener candle products.

Accordingly, it is an object of this invention to provide an air freshener candle product which releases air freshener into the atmosphere only under the pyrolysis conditions of the burning candle.

It is another object of this invention to provide a wick composition which has a content of air freshener constituent, and which is adapted for incorporation in a candle body.

It is a further object of this invention to provide a wick composition which can be produced by a continuous molding process.

Other objects and advantages of the present invention shall become apparent from the accompanying description and examples.

Publications of background interest relative to the present invention include U.S. Pat. Nos. 2,379,250; 2,829,511; 3,332,428; 3,499,452; 3,560,122; 3,705,890; 3,898,039; 4,092,988; 4,568,270; 5,538,018; and 5,569,779; incorporated by reference.

U.S. Pat. No. 2,829,511 describes a candle wick structure composed of a core strand of cellulose acetate in combination with an outer web of cotton fibers.

U.S. Pat. No. 5,538,018 describes a flavorant-release additive which is a cellulose derivative that is incorporated into a cigarette paper wrapper.

DESCRIPTION OF THE INVENTION

One or more objects of the present invention are accomplished by the provision of a wick composition comprising a polymeric strand which contains between about 0.5–40 weight percent of particulate air freshener-release cellulosic filler ingredient, wherein the air freshener is a chemically-bound constituent which is released into the atmosphere when the wick is combusted.

The wick composition typically is an elongated strand having a diameter between about 0.2–0.8 centimeters.

The polymeric matrix of an invention wick composition preferably is selected from the class of thermoplastic resins which in general are adapted for fiber-formation by processes such as extrusion or compression molding. It is preferred that the polymer is composed of elements which do not convert into noxious vapors under wick combustion conditions, such as carbon, hydrogen and oxygen.

Equipment and processes for polymer fiber-formation by extrusion are described in publications such as U.S. Pat. Nos. 3,065,502; 3,351,695; 3,577,588; 4,134,714; 4,302,409; and 5,320,798; incorporated by reference. A wick polymeric strand can be composed of multiple filaments.

Suitable fiber-forming polymers include hydrocarbyl polyolefinic derivatives such as low and high density polyethylene, low and high density polypropylene, polybutene, polystyrene, and the like.

Other types of suitable polymers include polyvinyl acetate, and acrylate resins such as polymethyl acrylate, polymethyl methacrylate, polybutyl methacrylate, poly (ethyl acrylate/ethylene), and the like.

Other preferred types of polymers include cellulosic derivatives such as cellulose acetate, methylcellulose, ethylcellulose, and the like.

Other types of polymers such as thermoset resins can be utilized by pressure molding a powder blend of resin and air freshener-release cellulosic filler. Other components can be included in a wick composition such as stearic acid or particulate polysaccharidic filler which does not contain chemically-bound air freshener, such as starch or guar gum.

The air freshener-release cellulosic filler ingredient of an invention wick composition typically is in the form of a powder, or in the form of fine fibers which have an average length between about 0.3–3 centimeters.

The cellulosic substrate of the filler ingredient can be obtained from vegetable sources such as cotton, linen, flax, hemp, jute, wood pulp, and the like. The cellulosic substrate can be in the form of substituted derivatives such as cellulose acetate or methylcellulose, which additionally have a content of chemically-bound air freshener constituent.

The term "cellulosic" as employed herein refers to a β-glucosidic polysaccharide corresponding to the formula:

$$[C_6H_7O_2(OH)_3]n$$

where n is an integer which provides an average molecular weight between about 100,000–2,000,000.

A present invention candle product can be produced by employing conventional candle making methods such as molding, dipping, and the like. The combustible body of a candle product typically is a thermoplastic blend of organic materials such as beeswax, paraffin wax, montan wax, carnauba wax, microcrystalline wax, fatty alcohols, fatty acids, fatty esters, natural and synthetic resins, and the like. Candle manufacture is described in publications such as "Modern Candle Making", A. Watt (Technical Press, London, 1935).

A wick normally extends longitudinally through a candle body. More than a single wick may be utilized in a spaced relationship, but usually a single wick component is centrally disposed in a shaped candle body. When a candle wick is ignited, the wick is adapted to combust gradually, so that both the wick and candle body are consumed.

When in a candle body, a present invention wick structure after ignition has sufficient porosity to absorb melted candlewax into the wick by capillary action for combustion during candle usage. The transport of melted wax can be enhanced by one or more capillary grooves extending axially along the surface of the wick filament.

A unique aspect of the present invention is the provision of a wick composition with an incorporated cellulosic filler ingredient which has a content of chemically-bound air freshener constituent.

The term "chemically-bound" as employed herein refers to a covalent bond between a cellulose polymer chain and an air freshener molecule, such as an ether or ester linkage. The Degree of Substitution (D.S.) can be between about 0.05–3.

The term "air-freshener" as employed herein is meant to include fragrances such as geraniol, insect repellents such as citronellal, and therapeutic agents such as menthol.

An air freshener constituent of a present invention wick composition can be any inherently volatile organic compound which is capable of being covalently linked to a cellulosic substrate by chemical reaction.

Suitable volatile air freshener compounds include alcohols such as undecanol, 4-isopropylcyclohexanol, geraniol, linalool, citronellol, farnesol, menthol, 3-trans-isocamphylcyclohexanol, benzyl alcohol, 2-phenylethyl alcohol, 3-phenylpropanol, 3-methyl-5-phenylpentanol, cinnamic alcohol, isoborneol, thymol, eugenol, isoeugenol, anise alcohol, methyl salicylate, and the like.

Other suitable air freshener compounds include aldehydes and ketones such as hexanal, decanal, 2-methyldecanal, trans-2-hexenal, acetoin, diacetyl, geranial, citronellal, methoxydihydrocitronellal, menthone, carvone, camphor, fenchone, ionone, irone, damascone, cedryl methyl ketone, muscone, civetone, 2,4-dimethyl-3-cyclohexene carboxaldehyde, 2-heptylcyclopentanone, cis-jasmone, dihydrojasmone, cyclopentadecanone, benzaldehyde, phenylacetaldehyde, dihydrocinnamaldehyde, cinnamaldehyde, α-amylcinnamaldehyde, acetophenone, benzylacetone, benzophenone, piperonal, and the like.

Other suitable air freshener compounds include esters such as trans-2-hexenyl acetate, allyl 3-cyclohexylpropionate, methyl cinnamate, benzyl cinnamate, phenylethyl cinnamate, and the like.

The chemical-bonding of an alcohol air freshener such as geraniol or menthol to a cellulose polymer can be accomplished by the formation of a carbonate ester linkage:

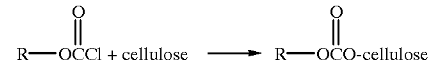

The reaction proceeds readily in the presence of a basic reagent such as sodium hydroxide or an organic amine. The production of cellulose carbonates are described in publications such as U.S. Pat. No. 3,705,890 and U.S. Pat. No. 5,068,321; incorporated by reference.

Another chemical means for forming a linkage between an alcohol air freshener and a cellulose polymer is by the use of an alcohol epichlorohydrin derivative under alkaline reaction conditions.

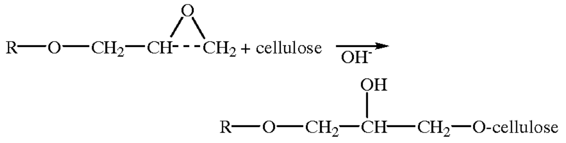

The chemical-bonding of an aldehyde such as citronellal or a ketone such as fenchone to a cellulose polymer can be accomplished by the formation of a hemiacetal (ketal) and/or acetal (ketal) linkage under acidic conditions:

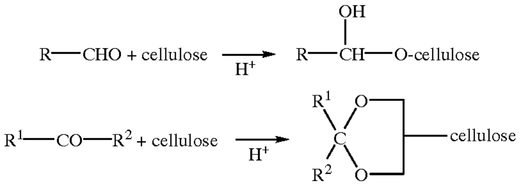

The chemical bonding of an ester such as phenylethyl cinnamate air freshener to a cellulose polymer can be accomplished by a Michael addition reaction under alkaline conditions:

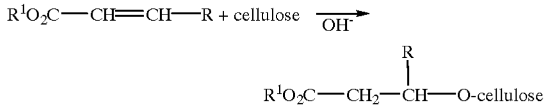

The Michael addition reaction is described in publications such as U.S. Pat. No. 2,415,040 and U.S. Pat. No. 5,569,779; incorporated by reference.

The chemical-bonding of an air freshener constituent in a present invention wick composition provides significant advantages not previously contemplated by the prior art.

The air freshener constituent is released only when the wick composition is being combusted. The air freshener is released by pyrolysis at a sustained constant rate.

The amount of air freshener constituent which is chemically-bound in the cellulosic substrate can be predetermined within a D.S. range between about 0.05–3 by selected synthesis conditions.

Because the air freshener constituent is chemically bound, there is no premature loss of air freshener by migration and evaporation. Also, since there is no air freshener such as a fragrance oil dispersed within a present invention candle product, the candle body does not soften and lose rigidity.

The present invention also contemplates a further embodiment in which a wick composition comprises a polymeric filament which contains between about 0.5–40 weight percent of particulate cellulosic filler, and which has one or more capillary grooves extending axially along the surface of the filament.

The following examples are further illustrative of the present invention. The components and specific ingredients are presented as being typical, and various modifications can be derived in view of the foregoing disclosure within the scope of the invention.

EXAMPLE I

This Example illustrates the preparation of geraniol glycidyl ether.

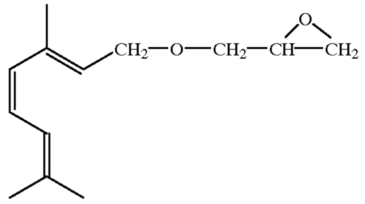

Geraniol (100 g) is added dropwise to a stirred mixture of 50% aqueous sodium hydroxide (300 mL), epichlorohydrin (300 g), and tetrabutylammonium hydrogen sulfate (60 g) with cooling to maintain a temperature of 20° C.

After a reaction period of 18 hours, the mixture is poured into water (one liter), and the aqueous medium is extracted with chloroform. The extract layer is washed with water, dried over sodium sulfate and filtered, and an oil product is recovered after solvent evaporation. NMR and IR confirm the structure.

EXAMPLE II

This Example illustrates the preparation of a polymeric wick composition which has a content of air freshener-release cellulosic filler in accordance with the present invention.

A reactor equipped with a reflux condenser and stirrer is charged with hexane (one liter), caustic solution (20 g of 50% aqueous sodium hydroxide), and cellulose fibers (30 g; 0.5 cm average length). The mixture is stirred for 30 minutes at 25° C. under a nitrogen atmosphere.

Geraniol glycidyl ether (50 g) is added to the slurry, and the resulting reaction mixture is heated at 75° C. for 10 hours. The mixture then is cooled to room temperature, neutralized with glacial acetic acid, and filtered.

The recovered cellulose fibers are washed with acetone and then with water. After drying, solid state NMR indicates that the cellulosic matrix has a D.S. of 0.35.

Polyethylene powder (MP 120° C.) is blended with 10 weight percent of the above described geraniol-substituted cellulose fibers, and the blend is passed through an extruder under heat and pressure to form a continuous strand of wick composition having a 0.35 cm diameter.

A cut section of the strand is ignited, and a flame persists until the wick section is completely consumed. The wick combustion releases a flowery rose aroma which is characteristic of geraniol.

A shaped paraffin candle (MP 63° C.) is drilled down the center, and a wick section is inserted. When the wick is ignited, a flame persists until the entire candle is consumed. A flowery rose aroma is released during the candle burning.

EXAMPLE III

This Example illustrates the preparation of a polymeric wick composition which has a content of fragrance-release cellulosic filler in accordance with the present invention.

Following the general procedure of Example I, glycidyl ethers are formed with the ingredients of a perfume oil:

| | Parts |
|---|---|
| hydroxycitronellal | 18.0 |
| cinnamyl alcohol | 1.7 |
| terpineol | 8.0 |
| benzylalcohol | 18.0 |
| phenethyl alcohol | 20.0 |
| linalool | 2.0 |

In a manner similar to that described in Example II, a slurry of cellulose powder is treated with the glycidyl ether mixture to chemically-bind the fragrance ingredients to the cellulosic matrix (a D.S. of 0.6).

Polystyrene powder (MP 150° C.) is blended with 20 weight percent of the above described fragrance-release cellulosic filler ingredient, and the blend is passed through an extruder under heat and pressure to form a continuous strand of wick composition having a 0.45 cm diameter.

A cut section of the strand is ignited, and a flame persists until the wick section is completely consumed. The wick releases a flowery lilac note. A similar fragrance release is obtained when the wick is burned within a candle wax body.

A similar result is obtained when the polymer ingredient is cellulose acetate or polyvinyl acetate.

EXAMPLE IV

This Example illustrates the preparation of menthyl chloroformate.

A reactor in a dry-ice/acetone bath (−75° C.) is charged with liquid phosgene (117 g). Menthol (130 g), dissolved in 500 mL of cyclopentane, is added dropwise to the phosgene with stirring. The reaction medium is refluxed for six hours at room temperature.

The excess phosgene and cyclopentane are removed under reduced pressure. The recovered menthyl chloroformate is dissolved in diethyl ether (300 mL), and the solution is washed with aqueous sodium bicarbonate, and then with distilled water. The liquid medium is dried over sodium sulfate, and the solvent is removed under reduced pressure to yield a purified menthyl chloroformate.

EXAMPLE V

This Example illustrates the preparation of a polymeric wick composition which has a content of menthol-release cellulosic filler in accordance with the present invention.

Cellulosic powder (400 g) is suspended in a blend of pyridine (1800 g) and benzene (3 liters), and the admixture is stirred for 20 hours at room temperature.

A 1200 g quantity of menthyl chloroformate is added dropwise to the stirred reaction medium at room temperature. The stirring is continued for 12 hours at a reaction medium temperature of 85° C. After cooling and filtering, the recovered cellulose powder is washed with benzene, then with isopropanol and with water. The wick product has a menthyl carbonate D.S. of 0.9.

Polypropylene powder (MP 110° C.) is blended with 4 weight percent of the above described menthol-release cellulosic filler ingredient, and the blend is passed through an extruder under heat and pressure to form a continuous strand of wick composition having a 0.3 cm diameter.

A cut section of the strand is consumed completely when ignited. A distinct aroma of menthol is detectable in the atmosphere during the wick burning. A similar menthol release is obtained when the wick is burned within a candle wax body.

EXAMPLE VI

This Example illustrates the preparation of a polymeric wick composition which has a content of citronellal-release celluosic filler in accordance with the present invention.

A reactor is equipped with a stirrer and a reflux condenser having a water-removal unit. The reactor is charged with benzene (500 mL), p-toluenesulfonic acid (50 mg), citronellal (50 g) and cellulose powder (30 g).

The admixture is heated at reflux with stirring, and continued until no more water is entrained as an azeotrope. After cooling, the acid catalyst is neutralized with ammonium hydroxide. The mixture is filtered, and the recovered cellulose powder is washed with water. After drying, solid state NMR indicates that the cellulosic matrix has a D.S. of about 0.2.

Polyethylene powder (MP 128° C.) is blended with 28 weight percent of the above described citronellal-release cellulosic filler ingredient, and the blend is passed through an extruder under heat and pressure to form a continuous strand of wick composition having a 0.6 cm diameter.

A cut section of the strand is consumed completely when ignited. A citronellal aroma is released during the wick burning. A similar citronellal release is obtained when the wick is burned within a candle body.

What is claimed is:

1. A wick composition comprising a polymeric strand which contains between about 0.5–40 weight percent of particulate air freshener-release cellulosic filler ingredient, wherein the air freshener is a chemically-bound constituent which is released into the atmosphere when the wick is combusted.

2. A wick composition in accordance with claim 1 which is produced by a continuous molding process.

3. A wick composition in accordance with claim 1 wherein the polymeric strand is a filament which has at least one capillary groove extending axially along the filament surface.

4. A wick composition in accordance with claim 1 wherein the polymeric strand comprises polyolefinic filament.

5. A wick composition in accordance with claim 1 wherein the polymeric strand is selected from the group consisting of polyethylene and polypropylene filaments.

6. A wick composition in accordance with claim 1 wherein the polymeric strand comprises cellulosic filament.

7. A wick composition in accordance with claim 1 wherein the polymeric strand comprises cellulose acetate filament.

8. A wick composition in accordance with claim 1 wherein the polymeric strand comprises multiple filaments.

9. A wick composition in accordance with claim 1 wherein the degree of air freshener substitution (D.S.) in the cellulosic filler ingredient is between about 0.05–3.

10. A wick composition in accordance with claim 1 wherein the air freshener constituent is chemically-bound by an ether linkage within the cellulosic filler ingredient.

11. A wick composition in accordance with claim 1 wherein the air freshener constituent is chemically-bound by an ester linkage within the cellulosic filler ingredient.

12. A wick composition in accordance with claim 1 wherein the air freshener constituent after release has a reconstituted alcohol group.

13. A wick composition in accordance with claim 1 wherein the air freshener constituent after release has a reconstituted carbonyl group.

14. A wick composition in accordance with claim 1 wherein the air freshener constituent after release has a reconstituted olefin group.

15. A wick composition in accordance with claim 1 wherein the air freshener constituent after release is a fragrance composition.

16. A wick composition in accordance with claim 1 wherein the air freshener constituent after release is an insect repellent composition.

17. A wick composition in accordance with claim 1 wherein the air freshener constituent after release is a therapeutic composition.

18. A wick composition in accordance with claim 1 wherein the released air freshener comprises geraniol.

19. A wick composition in accordance with claim 1 wherein the released air freshener comprises citronellal.

20. A wick composition in accordance with claim 1 wherein the released air freshener comprises menthol.

21. A wick composition in accordance with claim 1 which is an elongated strand having a diameter between about 0.2–0.8 centimeters, and which is adapted for incorporation in a candle product.

22. A wick composition comprising a polymeric filament which contains between about 0.5–40 weight percent of particulate cellulosic filler, and which has one or more capillary grooves extending axially along the surface of the filament.

23. A candle product having an axial wick component which comprises a polymeric strand which contains between about 0.5–40 weight percent of particulate air freshener-release cellulosic filler ingredient, wherein the air freshener is a chemically-bound constituent which is released into the atmosphere when the wick is combusted.

* * * * *